US00PP08957P

United States Patent [19]

Tistram

[11] Patent Number: Plant 8,957

[45] Date of Patent: Oct. 25, 1994

[54] SCABIOUS PLANT NAMED PINK MIST

[76] Inventor: David R. Tistram, Old Rectory, Binsted, Arundel, W. Sussex, BN18 OLL, England

[21] Appl. No.: 111,600

[22] Filed: Aug. 25, 1993

[51] Int. Cl.[5] ..... A01H 5/00

[52] U.S. Cl. ..... Plt./68.1

[58] Field of Search ..... Plt. 68.1

[56] References Cited

PUBLICATIONS

Anon, Trademarkscan search listing 'Pink Mist' from Dialog automated word search in file Trademarkscan files 126, 226, 246 performed Mar. 9, 1994.

*Primary Examiner*—James R. Feyrer

[57] ABSTRACT

A distinct cultivar of Scabious plant named Pink Mist, characterized by its distinctive pink flower color, large and dense inflorescences, prolific and continuous flowering, compact growth habit, and near sterility.

1 Drawing Sheet

1

The present invention relates to a new and distinctive cultivar of Scabious plant, botanically known as Scabiosa columbaria and referred to by the cultivar name Pink Mist.

The new cultivar is a color mutation from the nonpatented Scabious cultivar Butterfly Blue Beauty. The new cultivar was selected by me at Walberton Nursery in West Sussex, England, from a number of naturally-occurring mutants from Scabious cultivar Butterfly Blue Beauty.

Asexual reproduction of the new cultivar has shown that the unique features of this new Scabious are stabilized and are reproduced true to type in successive propagations.

The new cultivar has not been observed under all possible environmental conditions. The phenotype may vary significantly with variations in environment such as temperature, light intensity and daylength. The following observations, measurements, values, and comparisions describe plants grown at Walberton Nursery, West Sussex, England, under outdoor conditions or well-ventilated cold greenhouse conditions which closely approximate to those generally used in commercial horticulture and general garden practice.

The following characteristics have been repeatedly observed and are determined to be basic characteristics of Pink Mist, which in combination distinguish this Scabious from the wild forms of Scabiosa columbaria and distinguish it as a new and distinct cultivar:

1. The distinctive pink color of the flowers.
2. Larger and denser flower heads.
3. More prolific and continuous flowering.
4. More compact plant habit.
5. Its near sterility of flowers, seed is almost never formed.

The new cultivar is most similar to the nonpatented Scabious cultivar Butterfly Blue Beauty in its compact habit, continuous and prolific flowering, attractiveness to butterflies, and tolerance of both alkaline and acid soils. Pink Mist is principally distinguished from Butterfly Blue Beauty in its pink flower color in contrast to the blue-lavender flower color of Butterfly Blue Beauty.

The accompanying colored photographs illustrate the overall appearance and flower color of the new cultivar, showing the colors as true as it is reasonable possible to obtain in colored reproductions of this type.

2

The first photograph is a single plant of Pink Mist and the second a closer view of an individual inflorescence of Pink Mist, plants produced under warm night temperatures.

The following is a detailed description of my new cultivar based on plants produced under normal commercial practice in West Sussex, England, under outdoor conditions or well-ventilated cold greenhouse conditions with average day temperatures ranging from 7° to 18° C. and average night temperatures ranging from 2° to 10° C.

Color references are made to The Royal Horticultural Society Colour Chart except where general terms of ordinary dictionary significance are used.

Botanical classification: *Scabiosa columbaria* cv. Pink Mist.

Parentage: Naturally-occurring color mutant of Scabious cultivar Butterfly Blue Beauty.

Propagation:

A. *Type.*—By terminal tip cuttings and division.

B. *Time to initiate roots, summer.*—10 to 15 days at temperatures of 18° to 22° C.

C. *Time to initiate roots, winter.*—15 to 20 days at temperatures of 12° to 15° C.

D. *Rooting habit.*—Fibrous, branching.

Plant description:

A. *General appearance.*—Herbaceous perennial. Leaves frequenty persistent througout the winter. During cold temperatures or winter and early spring, rosette-forming with primary flower buds arising from the center of the rosette. Under warmer temperatures or during the summer, more divided leaves predominate with many flower stems arising from them.

B. *Foliage description.*—Basal or vegetative growth leaves: Numerous; opposite arrangement; typically 5 to 15 cm long by 2 to 4 cm wide; obovate to spatulate; lobed or coarsely toothed. Flower stem leaves: Arising from the axils of which flower buds arise; opposite arrangement, typically 4 to 10 cm long by 3 to 5 cm wide; pinnatifid or bi-pinnatifid. Texture, both type: Pubescent on top and under sides. Color, both types: Young foliage top side: 137C. Young foliage under side: 143C. Mature foliage top side: 137A. Mature foliage under side: 143A.

Flowering description:

A. *Flowering habit.*—Flowers borne in compound heads with outer florets larger than central ones.

B. *Natural flowering season.*—Natural flowering season is from April to November in the northern hemisphere.

C. *Quantity of flowers.*—One flower head per stem. Numerous inflorescences per plant.

D. *Flower stem description.*—Long, typically 15 to 40 cm, depending on temperature - longer under warmer temperatures greater than 25° C.; pubescent.

E. *Inflorescence.*—Shape: Flattened, round, often slightly irregular. Size: 4 to 6 cm in diameter. Floret color: Under warmer night temperatures of 15° to 20° C. floret color has more blue than red tones: Outer florets, top side: 75A. Outer florets, under side: 75B. Center florets: 75B. Under cooler night temperatures of 0° to 5° C., floret color has more red than blue tones: Outer florets, top side: 55B. Outer florets, under side: 55C. Center florets: 55C. Corolla: Typically 15 to 25 mm long on outer florets with petals unequal; 5 to 10 mm long on inner florets. Each corolla is surrounded by 5 bristles at its base. Involucral bracts: Typically 7 to 14 in one row; linear-lanceolate; held horizontally.

F. *Reproductive organs.*—Stamens: Typically R.H.S. 68D in color; frequently visible extending 2 to 5 mm above inflorescence in early stages of flowering. Pistils: White in color; clearly visible above the inflorescence in later stage of flowering. Seed: Normally absent, flowers are nearly sterile.

Disease resistance: Powdery Mildew is the only disease known to be a problem in the garden.

I claim:

1. A new and distinct Scabious plant named Pink Mist, as illustrated and described.

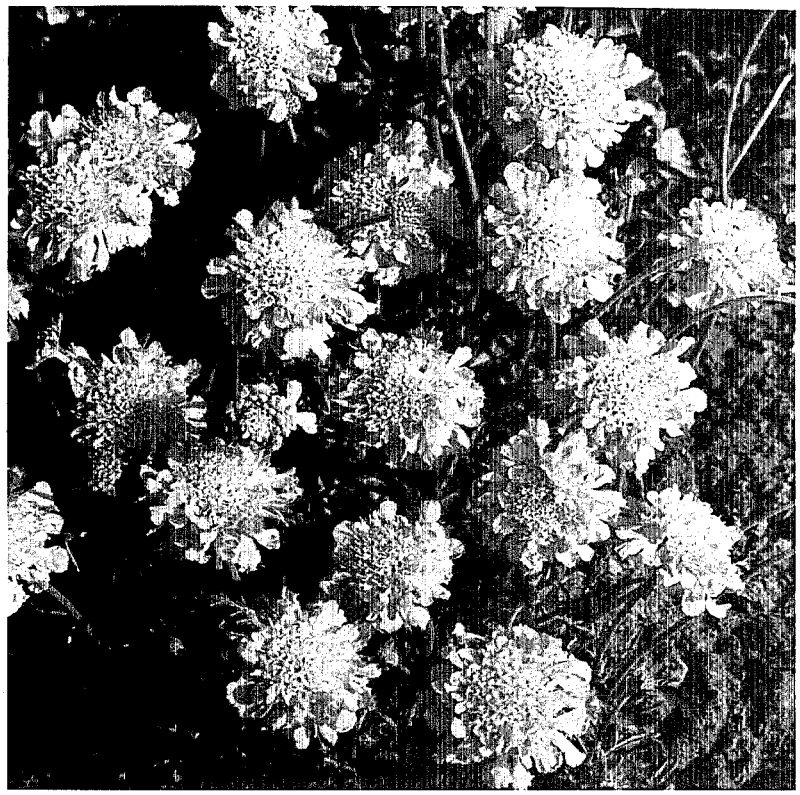
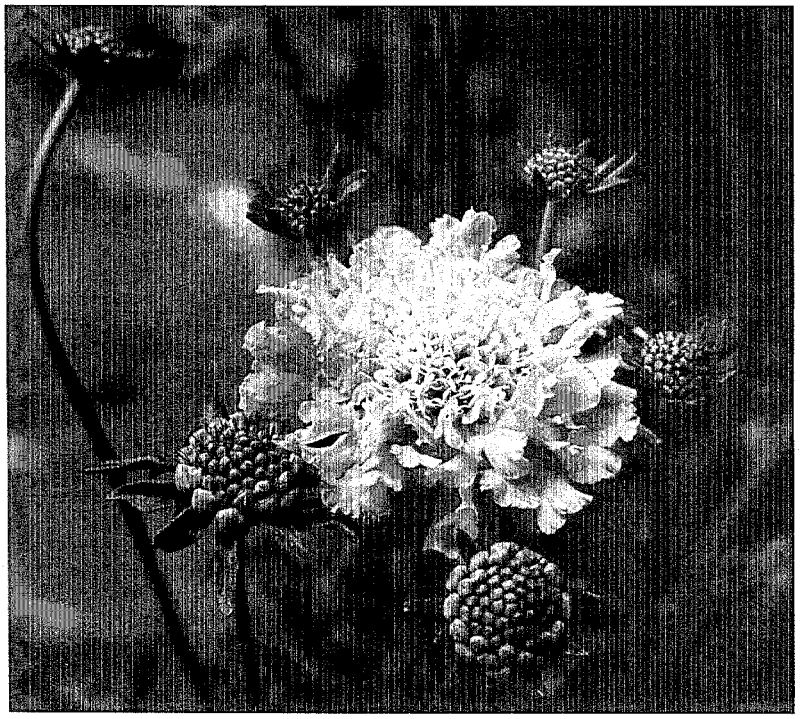

* * * * *